United States Patent [19]
Bakels et al.

[11] Patent Number: 5,800,497
[45] Date of Patent: Sep. 1, 1998

[54] MEDICAL ELECTRICAL LEAD WITH TEMPORARILY STIFF PORTION

[75] Inventors: Arnoldus P. Bakels, Simpelveld; Paul A. Gubbels, Brunssum; Nico M. Lokhoff, Kerkrade, all of Netherlands

[73] Assignee: Medtronic, Inc., Minneapolis, Minn.

[21] Appl. No.: 896,096

[22] Filed: Jul. 17, 1997

[51] Int. Cl.$^6$ .................................................. A61N 1/05
[52] U.S. Cl. ............................................................ 607/122
[58] Field of Search .................................. 607/119, 122, 607/123, 120, 121; 600/377, 374, 373

[56] References Cited

U.S. PATENT DOCUMENTS

| | | | |
|---|---|---|---|
| 5,207,219 | 5/1993 | Adams et al. | 128/419 D |
| 5,251,624 | 10/1993 | Bocek et al. | 607/6 |
| 5,265,600 | 11/1993 | Adams et al. | 607/4 |
| 5,267,559 | 12/1993 | Jin et al. | 128/419 D |
| 5,269,298 | 12/1993 | Adams et al. | 128/419 D |
| 5,279,291 | 1/1994 | Adams et al. | 607/5 |
| 5,282,836 | 2/1994 | Kreyenhagen et al. | 607/4 |
| 5,282,837 | 2/1994 | Adams et al. | 607/5 |
| 5,304,139 | 4/1994 | Adams et al. | 607/122 |
| 5,304,218 | 4/1994 | Alferness | 607/122 |
| 5,312,444 | 5/1994 | Bocek et al. | 607/5 |
| 5,332,400 | 7/1994 | Alferness | 607/5 |
| 5,348,021 | 9/1994 | Adams et al. | 128/708 |
| 5,350,402 | 9/1994 | Infinger et al. | 607/5 |
| 5,350,404 | 9/1994 | Adams et al. | 607/122 |
| 5,387,233 | 2/1995 | Alferness et al. | 607/126 |
| 5,395,373 | 3/1995 | Ayers | 607/8 |
| 5,403,354 | 4/1995 | Adams et al. | 607/5 |
| 5,433,729 | 7/1995 | Adams et al. | 607/5 |
| 5,441,519 | 8/1995 | Sears | 607/5 |
| 5,458,621 | 10/1995 | White et al. | 607/5 |
| 5,464,431 | 11/1995 | Adams et al. | 607/4 |
| 5,464,432 | 11/1995 | Infinger et al. | 607/5 |
| 5,464,433 | 11/1995 | White et al. | 607/5 |
| 5,476,498 | 12/1995 | Ayers | 607/122 |
| 5,509,888 | 4/1996 | Miller | 600/29 |
| 5,509,925 | 4/1996 | Adams et al. | 607/5 |
| 5,522,850 | 6/1996 | Yomtov et al. | 607/5 |
| 5,522,852 | 6/1996 | White et al. | 607/5 |
| 5,531,781 | 7/1996 | Alferness et al. | 607/122 |

Primary Examiner—Scott M. Getzow
Attorney, Agent, or Firm—Michael J. Jaro; Harold Patton

[57] ABSTRACT

A medical electrical lead which features a portion of the lead body which may be made temporarily stiff. The lead preferred is designed for implantation into a body and would include electrodes for both the ventricle and the atrium. The temporarily stiff portion may be located along the lead body in the area strictly within the atrium or may also include portions of the lead body implanted in the ventricle or even in the superior vena cava. The atrial portion further includes one or more electrodes. The temporarily stiff portion is formed through the use of a cavity in the lead body filled with magnet-rheologic fluid (hereinafter called "MRF"). Once the lead is implanted, a magnet may be used to communicate with the lead body and, in particular, with the MRF filled cavity. While in the magnetic field, the MRF will become solid and the lead body in such an area will become stiffer. The lead body, moreover, in this area will also be attracted to the magnet thereby causing the lead body in that portion to migrate towards the magnet. The MRF filled cavity may either be cylindrical in cross-section or have other cross-sections, such as a semi-circle. The temporarily stiff portion may be located anywhere along the lead body between the proximal and distal ends. In the preferred embodiment the temporarily stiff portion is located between approximately 0 and 20 cm from the lead distal end and is between approximately 2 cm and 20 cm in total length. In an additional embodiment the lead is disclosed for coronary sinus placement. Finally, a further embodiment is shown which features MRF for the transfer of force from a stylet to the lead.

17 Claims, 4 Drawing Sheets

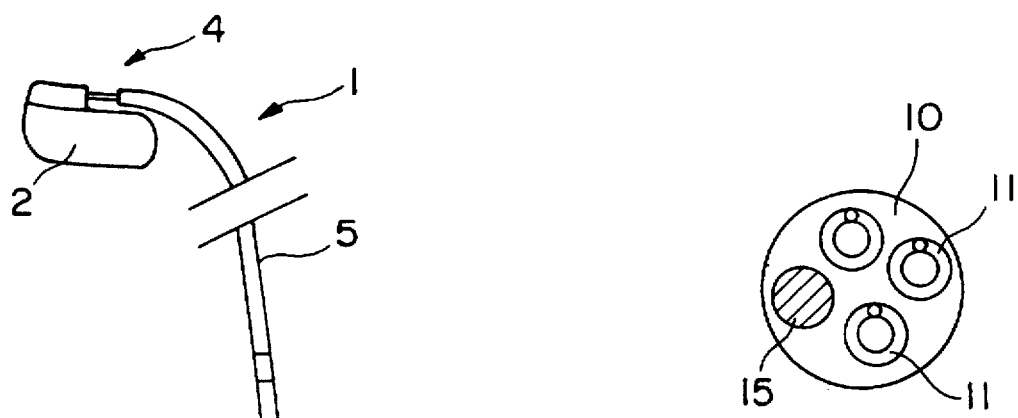
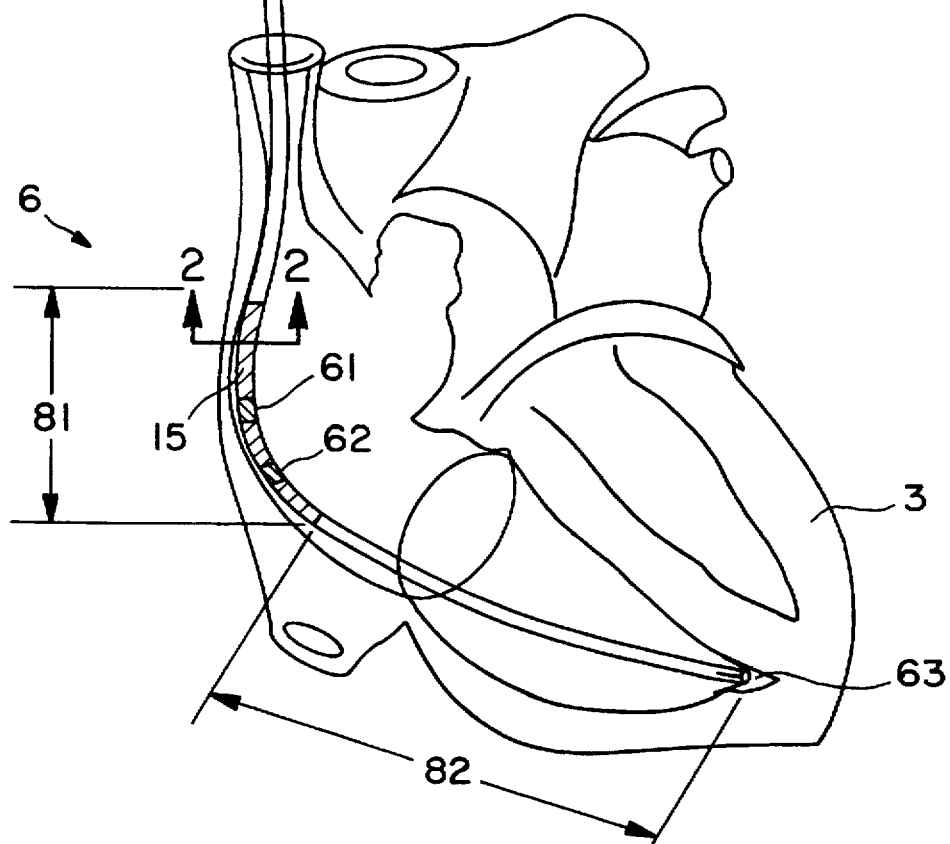
FIG. 2
FIG. 1

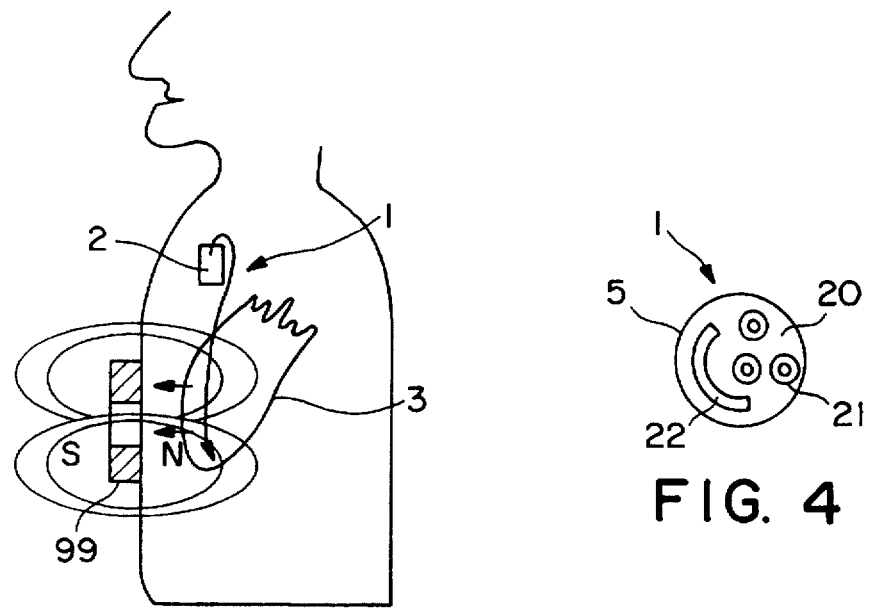
FIG. 3
FIG. 4
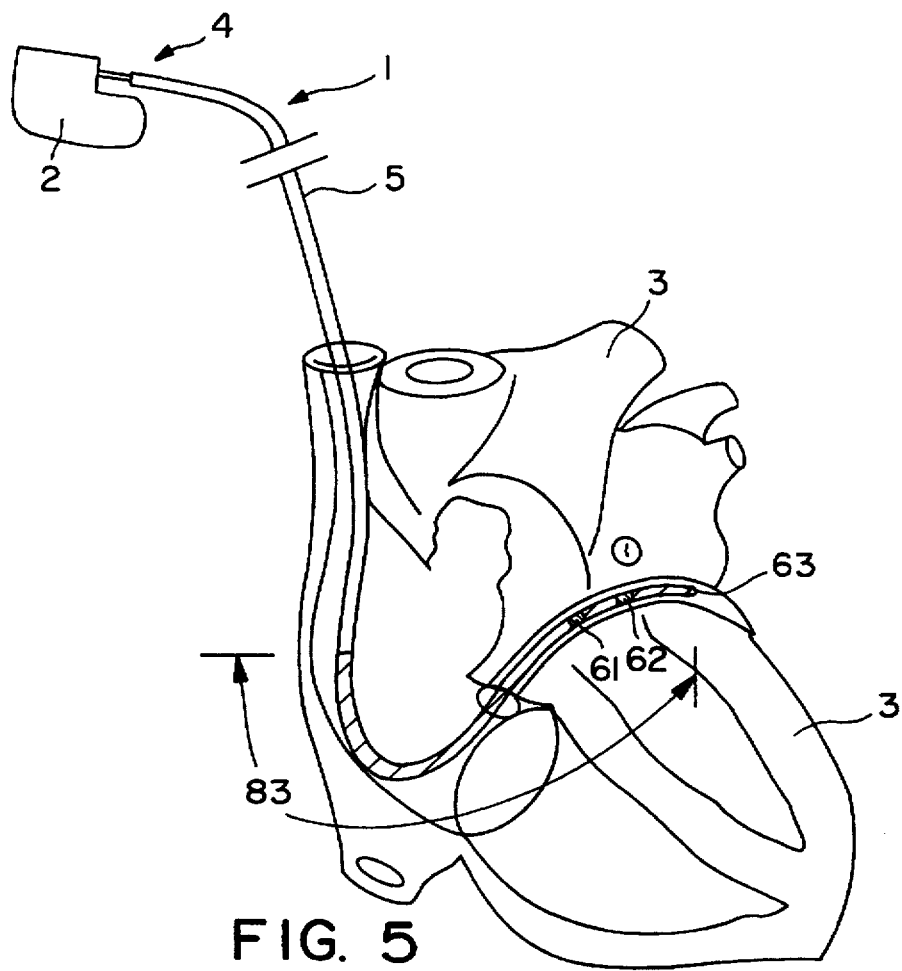
FIG. 5

MEDICAL ELECTRICAL LEAD WITH TEMPORARILY STIFF PORTION

FIELD OF INVENTION

The present invention relates to medical electrical leads and, more particularly, to medical electrical leads having a temporarily stiff portion.

BACKGROUND OF THE INVENTION

In the medical field, various types of body implantable leads are known and used. One type of commonly used implantable lead is an endocardial pacing lead.

Endocardial pacing leads are attached at their proximal end to an implantable pulse generator and at their distal end to the endocardium of a cardiac chamber. The distal end of an endocardial lead may engage the endocardium by either an active fixation mechanism or a passive fixation mechanism.

Active fixation mechanisms use a structure, such as helix or hook, to physically engage into or actively affix themselves onto the heart. Passive fixation mechanisms, such as a tine assembly, lodge or passively fix themselves to the heart.

One problem common to all such fixation systems, however, is to reliably fix such a lead in the atrial chamber. The atrium, unlike the ventricle, is relatively smooth in its interior. Thus, passive fixation systems, such as tines, are not able to reliably engage into structures along the interior portion of the atrium. The atrial chamber, moreover, is also generally thin. This means that there is not a large, meaty, portion of tissue available for an active fixation device to engage with.

Others have attempted to provide leads which may be adequately fixed into the atrium, these, however, have met with limited success. Gold, U.S. Pat. No. 4,454,888 provided a J-shaped atrial lead in which the pre-bent J-portion of the lead was formed using a separate metallic strip. During chronic use, however, this metallic strip often dislodged or separated from the lead body upon which it presented a sharpened metal barb to the tissues. Not surprisingly, this unfortunately had catastrophic consequences for the patients. Another approach to electrode placement within the atrium may be seen in the patent of Riestriena U.S. Pat. No. 4,401,126 which discloses a lead body having various loops and stiffness of the lead body in the atrium. This design, however, has several drawbacks, including it being difficult to implant and properly position the loop containing the electrodes, as well as the lead body being permanently stiff in the area of the atrium. Permanent stiffness of the lead body in the area of the atrium may have several drawbacks. First, because the lead is extra stiff in the area of the atrium and the atrium is not the most strong portion of the heart, the stiffened lead body may not permit the atrium to fully contract when such a lead is implanted. This can cause a hemodynamic insufficiency or impair cardiac output. Moreover, when a stiffened body is placed within the atrium the heart muscle may develop, in response to the object, so as to contract with greater force in the area. This increased area of heart tissue, often called cardiomyopathy, may have untoward effects on the conduction pathways, also contributing to diminished cardiac output.

SUMMARY OF THE INVENTION

The present invention concerns a medical electrical lead which features a portion of the lead body which may be made temporarily stiff. The lead preferred is designed for implantation into a body and would include electrodes for both the ventricle and the atrium. The temporarily stiff portion may be located along the lead body in the area strictly within the atrium or may also include portions of the lead body implanted in the ventricle or even in the superior vena cava. The atrial portion further includes one or more electrodes. The temporarily stiff portion is formed through the use of a cavity in the lead body filled with magnet-rheologic fluid (hereinafter called "MRF"). Once the lead is implanted, a magnet may be used to communicate with the lead body and, in particular, with the MRF filled cavity. While in the magnetic field, the MRF will become solid and the lead body in such an area will become stiffer. The lead body, moreover, in this area will also be attracted to the magnet thereby causing the lead body in that portion to migrate towards the magnet. The MRF filled cavity may either be cylindrical in cross-section or have other cross-sections, such as a semi-circle. The temporarily stiff portion may be located anywhere along the lead body between the proximal and distal ends. In the preferred embodiment the temporarily stiff portion is located between approximately 0 and 20 cm from the lead distal end and is between approximately 2 cm and 20 cm in total length. In an additional embodiment the lead is disclosed for coronary sinus placement. Finally, a further embodiment is shown which features MRF for the transfer of force from a stylet to the lead.

BRIEF DESCRIPTION OF THE DRAWINGS

FIG. 1 is a view of a system featuring a lead of the present invention.

FIG. 2 is a cross-sectional view of the lead body shown in FIG. 1.

FIG. 3 is a side view showing a lead implanted within a patient and a magnet used to stiffen the lead body.

FIG. 4 is a alternate embodiment of the lead shown in FIG. 1.

FIG. 5 is an alternate embodiment of a lead which is designed for implantation in the coronary sinus.

Figure 6:
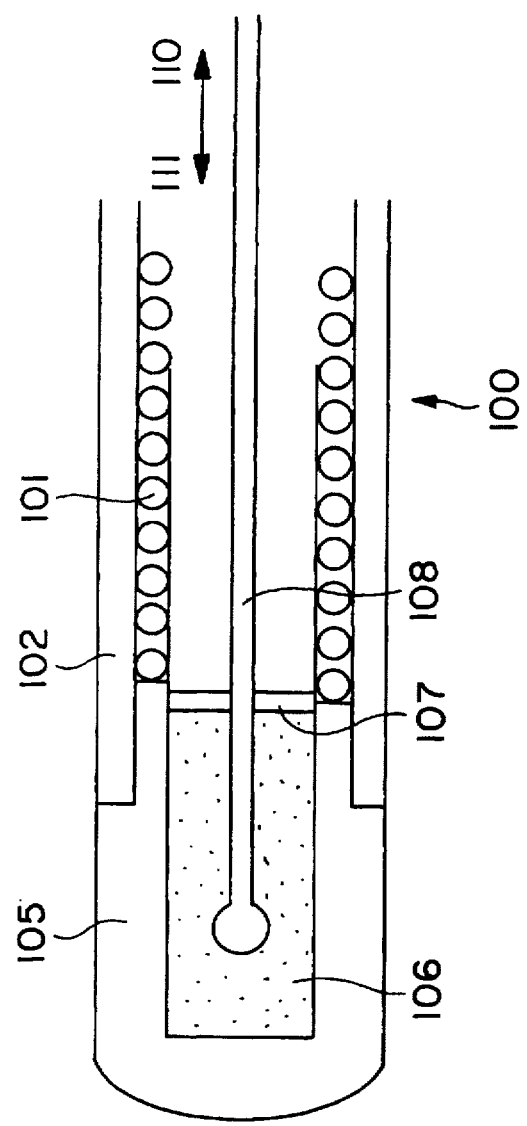
FIG. 6 is an alternative embodiment of a lead.

The FIGS. are not necessarily to scale.

DETAILED DESCRIPTION OF THE DRAWINGS

It is to be understood, that the present invention is not limited to use only in introducing atrial or ventricular pacing leads, and may be employed in introducing many of various types of therapeutic or diagnostic devices including transvenous leads intended to be disposed at various places within patient, including, for example, leads intended to be disposed within the patient's coronary sinus, as well as various other types of electrical leads, including nerve, muscle or defibrillation leads. It is to be further understood, moreover, the present invention may be employed in introducing many of various types of therapeutic or diagnostic catheters and is not limited only to the introduction of electrical leads. For purposes of illustration only, however, the present invention is below described in the context of the introduction of endocardial pacing leads. The term "lead," however, is used in the broadest possible manner and should be read to include any elongated medical device.

FIG. 1 is a view of a lead of the present invention. As seen, lead 1 is used to couple an implantable pulse generator 2 to a heart 3. Implantable pulse generator as used herein refers to any device which provides electrical stimulation therapy to a body tissue or organ and is not intended to merely be limited to a so-called pacemaker. In the preferred embodiment, however, implantable pulse generator comprises any dual chamber model selected from the Medtronic Thera series of pacemakers. As seen, lead 1 has essentially three portions, a connector pin assembly 4, a lead body 5 and an electrode portion 6. Connector pin assembly 4 is of any standard design suitable for use of coupling the lead to an implantable medical device such as those connectors conforming to the IS-1 standard, to name an example. Lead body 5 is constructed from an insulative sheath 10 and one or more conductors 11, as best seen in FIG. 2. Electrode portion 6 of lead body features a pair of electrode 61, 62 spaced apart a distance 8.6 mm. Further details concerning atrial electrodes as well as the tip electrode 63 which may be used can be found in the U.S. Pat. No. 5,628,778 "Single Pass Medical Electrical Lead" of Kruse et al. assigned to the assignee of the present invention and incorporated herein by reference. As discussed in more detail below, the electrode portion of the lead body features one or more cavities containing MRF fluid. Thus, when the MRF is made solid through the presence of a magnetic field, the corresponding section of the lead body will become stiffer. As seen in this embodiment the MRF 15 extends for a length 81 at a distance 82 from the distal end of the lead. In the preferred embodiment both length and distance are approximately 8 cm. Of course, each dimension may vary, it is conceived the cavity containing MRF may extend for a length of approximately 2-20 cm at a distance from approximately 0-20 cm from the distal end of the lead. Moreover, although a single MRF cavity is illustrated, multiple cavities containing MRF may also be implemented, as shown below.

FIG. 2 is a cross-section of the lead body shown in FIG. 1. As mentioned above, lead body is constructed from an insulated polymer sheath 10 and one or more conductors 11. In the preferred embodiment sheath is silicone and has four cylindrical cavities running at least within a portion of the length of the sheath. Positioned along the length of three such cavities are the conductors. In the preferred embodiment conductors are coiled multi-filar conductors of a biocompatible alloy such as MP35N. Although shown as coiled conductors it should be understood other devices of conductors may also be used such as bundle stranded wires. Moreover, the coiled design of the conductors as well as their cross-sections may also be varied if desired. As seen, a fourth lumen within the sheath is filled with MRF 15. As discussed above, MRF is a material which normally exists in a liquid form, but, in the presence of a sufficiently intense magnetic field, will act as a solid. The particular intensity necessary to achieve the desired transformation of the MRF from liquid to solid depends upon the particular MRF used. In the preferred embodiment the MRF is model MRF 32 LD, a silicone oil based MRF available from Lord Corporation, 405 Gregson Drive, Cary, N.C., U.S.A.

FIG. 3 is a side view showing a lead according to the present invention implanted within a patient having a magnet placed in proximity to thereby cause the lead body to stiffen. As discussed above, the MRF solidifies when in the presence of a magnet 99. The lead according to the present invention features a portion of the lead body having MRF therein. When such a lead is placed in the presence of a magnetic field the MRF will solidify causing the lead body flex characteristics to thereby also solidify or stiffen. Through such a design, the lead body will be drawn against the heart wall in the direction shown thereby causing the electrodes to become in better contact with the heart tissue. Moreover, due to the increased stiffness of the lead body in this portion, the heart tissue will be aggravated by the temporarily stiff lead body thereby accelerating the growth of fibrotic tissue in this area. Ultimately, such fibrotic tissue growth will act to fix or couple, through such tissue, the lead body, and thus the nearby electrodes, to the heart. Long term, this means the lead is better coupled to the previously uncoupleable atrial tissue. In addition, the lead body in this area will also be attracted to the magnet thereby causing the lead body in that portion to migrate towards the magnet and further assist in the optimal contact of the electrodes to the heart tissue. Once sufficient fibrotic tissue growth is seen, then the magnetic field is removed and the lead body again goes into a relatively more flexible or flaccid disposition. The magnetic field may be provided using either a conventional magnet or some sort of electromagnet, whichever is preferred. As discussed above, the particular intensity necessary to achieve the desired transformation of the MRF from liquid to solid depends upon the particular MRF used. Moreover, because implantable pulse generators typically utilize magnetic reed switches it is further comprehended that a second magnet (not shown) may be provided in the vicinity of the pulse generator to prevent the lead body stiffened magnet to reset or trip reed switch in the pulse generator.

FIG. 4 is a alternative embodiment of the lead shown in FIG. 1. In particular, in this FIG. the lead shown in FIG. 1 is entirely the same but for a varied cross-section of the lead body. As seen in this embodiment, the lead body is an insulative sheath 20 having a series of three lumens 21 being circular in cross-section with a fourth lumen 22 being semi-circular in cross-section. Through such a cross section the flex characteristics of the lead body in the vicinity of the MRF may be changed, in particular, the lead body may be made to become more stiff due to the MRF as compared to a simple cylinder filled with MRF. Moreover, although the semi-cylindrical shape is shown, other shapes may be used, such as squares, ellipses, rectangles or any combination thereto.

FIG. 5 is an alternative embodiment of a lead design for implantation in the coronary sinus. As seen the lead body in this embodiment features an MRF portion which extends from the distal end of the lead for an amount preferably between 12-15 cm so that it extends, in a patient, from the SVC to the great vein. Through this design the distal portion of the lead body may be stiffened using a magnet to thereby increase the ease of insertion of the lead in the coronary sinus. In this embodiment the lead further features a distal type electrode as well as two ring electrodes of a design well known in the art.

FIG. 6 is an alternative embodiment of a lead. In this embodiment MRF is used so as to enhance the ability of a stylet to control the end of the lead without necessitating any complex stylet lead interlocks. As seen lead 100 is constructed in a typical fashion, featuring coiled conductor 101 and insulative sheath 102. Both sheath and conductor may be fabricated from any desired material, such as silicone and MP35N respectively to name an example. Positioned on the distal end of lead is distal cap assembly 105. Distal cap assembly feature a cavity filled with MRF 106. Distal cap assembly further features a valve 107 so as to maintain the MRF while in the fluid state within cavity. Valve may be of any design such that a stylet 108 may be introduced therethrough and into the MRF. In the embodiment shown valve comprises a annular flap of silicone having a hole therethrough. Stylet features a bulb at its distal end. Bulb increases the amount of friction between the MRF and the stylet once the MRF is made solid. This permits the stylet to be pulled in the direction 110 or pushed in the direction 111 so as to better enable MRF and stylet to manipulate the lead. As described above, MRF is only solid within the presence of a sufficient magnetic field. Thus, once the magnet is removed, then stylet may be easily removed from MRF 106. Although not illustrated, it is quite possible to make the stylet itself electromagnetic such that the stylet could be used to modify the state of the MRF.

Figure 7:
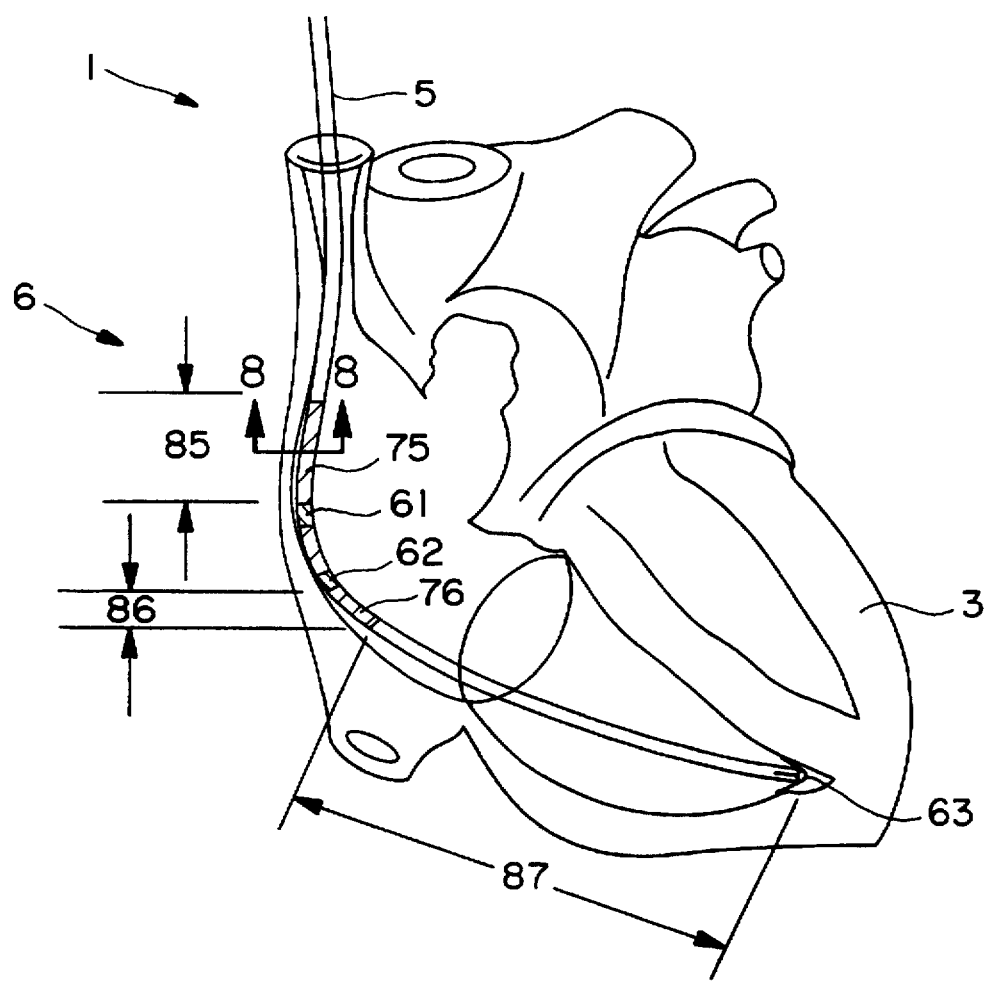
FIG. 7 is a alternate embodiment of the lead shown in FIG. 1.

FIG. 7 is an alternative embodiment of the present invention. In this FIG. only the distal half of lead 1 is shown, although connector pin assembly is the same as that discussed above. In this embodiment electrode portion 6 of lead body 5 feature a pair of cavities 75, 76 containing MRF fluid. Cavity 75 extends for a length 85 of between approximately 1-10 cm with approximately 4 cm preferred. Cavity 76 extends for a length 86 of between approximately 1-10 cm with approximately 4 cm preferred. As seen each cavity borders an electrode 61, 62 which function as a bipolar electrode for use in stimulating and sensing the heart. As discussed above, electrodes may be constructed in any suitable fashion known in the art. The electrodes are spaced apart a distance 8.6 mm. Further details concerning atrial electrodes which may be used can be found in the U.S. Pat. No. 5,628,778 "Single Pass Medical Electrical Lead" of Kruse et al. assigned to the assignee of the present invention and incorporated herein by reference.

Figure 8:
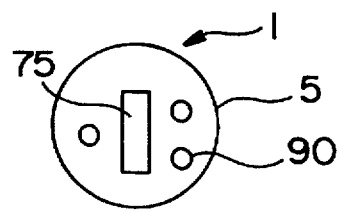
FIG. 8 is a cross-sectional view of the lead body shown in FIG. 7.

FIG. 8 is a cross sectional view across line 8—8 of the lead body shown in FIG. 7 As seen in this embodiment the MRF containing cavity 75 is rectangular in cross section. Although only one cavity is shown in this view, the other cavity 76 is also rectangular in shape. In this embodiment the conductors 90 used are fashioned from HBSW wire of MP35N.

Although a specific embodiment of the invention has been disclosed, this is done for the purposes of illustration and is not intended to be limiting with regard to the scope of the invention. It is contemplated that various substitutions, alterations, and/or modifications, including but not limited to those specifically discussed herein, may be made to the disclosed embodiment of the invention without departing from the spirit and scope of the invention as defined in the appended claims, which follow.

What is claimed is:

1. A medical electrical lead comprising:
   a lead body, the lead body having a first portion and a second portion, the lead body further having an insulative sheath and a conductor, the insulative sheath having a first end and a second end, the conductor positioned within the insulative sheath and extending between the first end and the second end;
   means for temporarily making a first portion of the lead body more stiff by exposing the first portion to a magnetic field; and
   an electrode positioned near the second end, the electrode coupled to the conductor.

2. A medical electrical lead according to claim 1 wherein the means for temporarily making a first portion of the lead body more stiff comprises a first cavity in the first portion of the lead body, the first cavity containing a first amount of MRF.

3. A medical electrical lead according to claim 2 wherein the first cavity is within the insulative sheath.

4. A medical electrical lead according to claim 2 wherein the first cavity comprises a cylindrical cavity.

5. A medical electrical lead according to claim 4 wherein the cylindrical cavity is within the insulative sheath.

6. A medical electrical lead according to claim 2 wherein the first cavity is located approximately 8 cm from the distal tip.

7. A medical electrical lead according to claim 2 wherein the first cavity is approximately 8 cm long.

8. A medical electrical lead comprising:
   a lead body, the lead body having a first portion and a second portion, the lead body further having an insulative sheath and a conductor, the insulative sheath having a first end and a second end, the conductor positioned within the insulative sheath and extending between the first end and the second end;
   a stylet positioned extending from a first end of the lead body into an interior portion of the lead body
   means for temporarily permitting the longitudinal transfer of force between the stylet and the lead body by exposing the lead body to a magnetic field.

9. A medical electrical lead according to claim 8 wherein the lead body has at least a first cavity in the first portion, the first cavity containing a first amount of MRF.

10. A medical electrical lead comprising:
    a lead body, the lead body having a first portion and a second portion, the lead body further having an insulative sheath and a conductor, the insulative sheath having a first end and a second end, the conductor positioned within the insulative sheath and extending between the first end and the second end;
    means for temporarily making the first portion of the lead body more stiff by exposing the first portion to a first magnetic field;
    means for temporarily making the second portion of the lead body more stiff by exposing the second portion to a second magnetic field; and
    an electrode positioned near the second end, the electrode coupled to the conductor.

11. A medical electrical lead according to claim 10 wherein the means for temporarily making a first portion of the lead body more stiff comprises a first cavity in the first portion of the lead body, the first cavity containing a first amount of MRF.

12. A medical electrical lead according to claim 10 wherein the means for temporarily making a second portion of the lead body more stiff comprises a second cavity in the second portion of the lead body, the second cavity containing a first amount of MRF.

13. A medical electrical lead according to claim 12 wherein the first cavity is within the insulative sheath.

14. A medical electrical lead according to claim 12 wherein the first cavity comprises a cylindrical cavity.

15. A medical electrical lead according to claim 14 wherein the cylindrical cavity is within the insulative sheath.

16. A medical electrical lead according to claim 12 wherein the first cavity is located approximately 8 cm from the distal tip.

17. A medical electrical lead according to claim 12 wherein the first cavity is approximately 8 cm long.

* * * * *